United States Patent
Weisenberger et al.

(10) Patent No.: US 9,213,023 B2
(45) Date of Patent: *Dec. 15, 2015

(54) BUILDING MOISTURE CONTENT CERTIFICATION SYSTEM AND METHOD

(75) Inventors: Andrew R. Weisenberger, New York, NY (US); Robert A. Weisenberger, New York, NY (US)

(73) Assignee: SAVANNAH IP. INC., Milwaukie, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 10/621,860

(22) Filed: Jul. 16, 2003

(65) Prior Publication Data

US 2005/0011255 A1 Jan. 20, 2005

(51) Int. Cl.
*G01N 5/02* (2006.01)
*G01N 33/46* (2006.01)
*G01N 33/38* (2006.01)
*G06Q 30/00* (2012.01)

(52) U.S. Cl.
CPC ............... *G01N 33/46* (2013.01); *G01N 33/38* (2013.01); *G06Q 30/018* (2013.01)

(58) Field of Classification Search
CPC ........ G01N 5/02; G01N 5/025; G01N 27/048
USPC .............................................. 73/73; 324/640
See application file for complete search history.

(56) References Cited

U.S. PATENT DOCUMENTS

| | | | |
|---|---|---|---|
| 4,775,944 A * | 10/1988 | Nakamura | 700/277 |
| 5,004,483 A | 4/1991 | Eller et al. | |
| 5,212,958 A | 5/1993 | Anderson | 62/150 |
| 5,259,553 A * | 11/1993 | Shyu | 236/49.3 |
| 5,992,161 A | 11/1999 | O'Halloran et al. | 62/90 |
| 6,340,892 B1 * | 1/2002 | Rynhart et al. | 324/640 |
| 6,402,613 B1 | 6/2002 | Teagle | |
| 6,705,939 B2 * | 3/2004 | Roff | 454/185 |
| 8,567,688 B2 | 10/2013 | Weisenberger et al. | |
| 2003/0040934 A1 * | 2/2003 | Skidmore et al. | 705/1 |
| 2004/0190586 A1 * | 9/2004 | Lee et al. | 374/5 |
| 2014/0020261 A1 | 1/2014 | Weisenberger et al. | |

FOREIGN PATENT DOCUMENTS

CA 2447389 A1 1/2005
JP 2002317560 A * 10/2002

OTHER PUBLICATIONS

"Moisture Testing Guide for Wood Frame Construction Clad With Exterior Insulation and Finish Systems (EIFS)", 31 pages, from www.toolbase.org/Docs/MainNav/MoistureandLeaks/876_protocol5A.pdf?TrackID=&CategoryID=1013&DocumentID=876, Aug. 4, 1998.*

"Testing Housing Materials for Moisture", 2 pages, from www.extension.umn.edu/info-u/household/BK270.html, Copyright 1998.*

(Continued)

*Primary Examiner* — Hezron E Williams
*Assistant Examiner* — Rodney T Frank
(74) *Attorney, Agent, or Firm* — Schwabe Williamson & Wyatt

(57) ABSTRACT

A moisture content level certification system and method involves taking moisture content measurements within a structure and issuing a certificate of moisture content level. Moisture content level pass/failure certifications may also be issued.

20 Claims, 2 Drawing Sheets

(56) References Cited

OTHER PUBLICATIONS

"Indoor Air Quality Monitors", Quest Technologies PDF Brochure for Model AQ 5000 Hand Held IAQ Monitor and Model AQ 5001 Portable IAQ Monitor, Rev. A Apr. 2000.*
ASTM, (1998), D4444-92e1 standard test methods for use and calibration of hand-held moisture meters, American Society for Testing and Materials; abstract obtained from http://alcor.concordia.ca/~raojw/crd/reference/reference000784.html.*
Data and brochure sheets for the Quest Technologies Indoor Air Quality Monitors models aq-5000 and aq-5001. A brief summary of the devices can be found at the following web site addresses: http://www.quest-technologies.com/IAQ/aq5000.htm and http://www.quest-technologies.com/IAQ/aq5001.htm.*
U.S. Appl. No. 60/453,856 for establishement of priority over the present application.*
Harriman III et al. article, "Preventing Mold by Keeping New Construction Dry", ASHRAE Journal, Sep. 2002, obtained via http://www.floodrentals.com/images/Preventing_Mold_In_New_Construction.pdf.*
Mold in Your Home, 6 pages, from www.residentialinspections.com, copyright 2001, Residential Inspections LLC. Publication date unknown.
Solutions—Munters Keeps Construction Projects on Schedule! Munters 2000/2001.
Preventing Mold by Keeping New Construction Dry. Harriman, Schnell & Fowler, p. 28-34, ASHRAE Journal, Sep. 2002.
Preventing Mold by Keeping New Construction Dry. Harriman, Schnell & Fowler, presented at the 2001 ASHRAE IAQ seminar. 2001.
Construction Drying, Munters Oct. 2000.
Using Desiccant Technology to End Moisture Nightmare on Construction Projects, Munters, Feb. 21, 2002.
Moisture Intrusion and Inspection, 2 pages, from www.residentialinspections.com, copyright 2001, Residential Inspections LLC. Publication date unknown.
Mold in Your Home, 5 pages, from www.residentialinspections.com, copyright 2001, Residential Inspections LLC. Publication date unknown.
Wood Moisture Content, Clemson Extension Residential Housing, HL 255, Rev. p. 1-2, Rev. Apr. 1997.
Willis, "Creating a Little Desert Indoors—Dehumidifiers Speed Up Finish Work Inside NW Buildings", Jun. 1, 2000, Daily Journal of Commerce.
Munters, "Case Study—Construction Drying: Mold and Mildew Protection Project Yields Multiple Benefits Round Rock, Texas", Mar. 2002.
Harriman et al., "Preventing Mold by Keeping New Construction Dry", ASHRAE Meeting, Jan. 2003, Chicago, IL.
Archive Press Release, "Munters New HCU Product Allows Dehumidity Control Independently of Temperature Control", http:/News.thomasnet.com/fullstory/7783, Mar. 8, 2002.
Stolowitz Ford Cowger LLP, "Listing of Related Cases", May 22, 2014, 1 page.

* cited by examiner

BUILDING MOISTURE CONTENT CERTIFICATION SYSTEM AND METHOD

BACKGROUND OF THE INVENTION

This invention relates to certification of buildings and construction, and more particularly to a system and method for certifying buildings to have an identified moisture content level to identify the probability of mold growth claims or moisture damage claims against a builder or owner.

Mold, mildew and water problems in buildings are becoming more common, and can lead to substantial remediation efforts, with associated costs or litigation.

In any structure problems can arise if a particular level of moisture content exists. Mold will typically grow in wood or other organic construction material above a certain moisture content. Thus, mold can grow in construction material if sufficient moisture is present in the structure components. Apart from mold, moisture damage to the structure or components thereof may result from moisture.

Should mold or other moisture related damage develop, it is often detected immediately, or sometimes such detection is delayed. In some cases, it is never detected.

Mold and moisture remediation and prevention of future growth, is costly and time consuming. The existence of mold and moisture damage in a structure can cause public relations issues, wherein the builder or owner can be equated with the bad publicity related to the mold and moisture damage issues. Still further, legal issues can arise, related to the costs and delay of remediation, alleged health issues from occupants of the affected buildings, and contractual disputes arising over purchase or lease of the affected property, as a purchaser might wish to cancel a property transaction based on the mold issues.

Financing and monetary requirements often demand that structures be built as quickly as possible, to minimize the duration of construction financing, for example, and to increase construction related revenue. Such time constraints result in framing being covered up as quickly as possible. These time constraints do not allow a builder to have a partially completed structure sit for days or weeks to allow any moisture in the construction materials to naturally reach equilibrium with the moisture in the environment, and this increases the likelihood that moisture may be sealed up, leading to a higher likelihood of mold growth occurring. Depending on climate factors, the business cycle of construction may not allow sufficient time for waiting for the natural drying process. Thus, the likelihood that a building may have excessive moisture content is increased. The presence of moisture and/or mold may also impact the ownership, use, financing, insurability, refinancing and sale of structures.

In sales of homes or structures, both sellers and purchasers may be unaware of moisture content within the structure.

Heretofore, the issue of moisture content in a building has been addressed as an afterthought in reactive fashion. There has been no organized manner or system to examine and consider the moisture content of a building and or to certify this moisture state.

SUMMARY OF THE INVENTION

In accordance with the invention, a certification system and method is provided for addressing the issue of moisture content in a structure. In accordance with the system, a moisture content level determination is made and a certificate is issued to show moisture content.

Accordingly, it is an object of the present invention to provide an improved method for determining and certifying moisture content levels in construction projects.

It is a further object of the present invention to provide an improved system for determining and certifying of moisture content.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION

The invention according to a preferred embodiment comprises a system and method for certifying a structure to have a moisture content. The certification may include certifying that moisture content levels have been measured, and may include a report of the measurement data that was actually recorded during the certification measurement phase.

Figure 1:
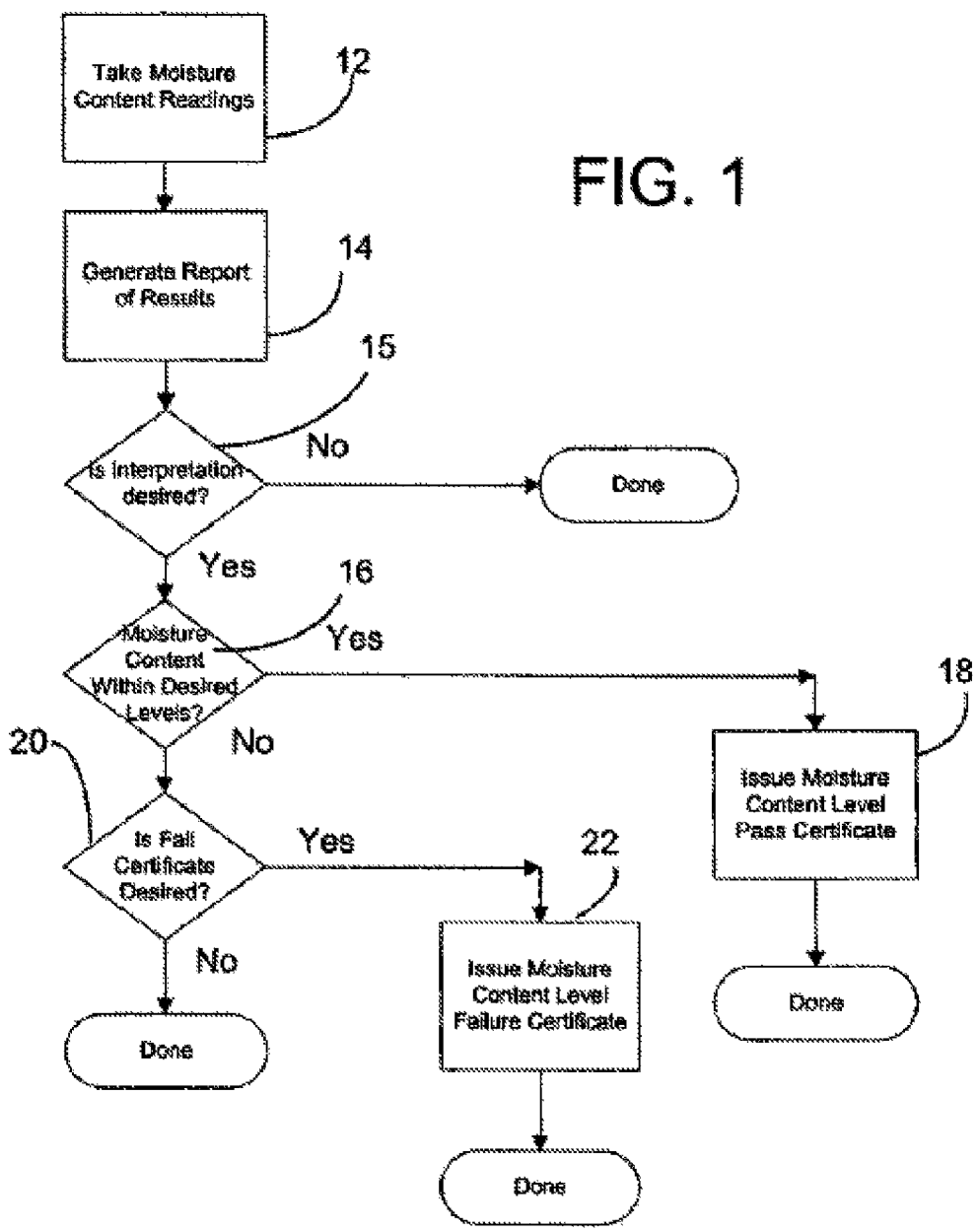
FIG. 1 is a block diagram of the process according to the present invention.

Referring now to FIG. 1, which is a block diagram of the moisture level certification process according to the present invention, initial readings of moisture content as well as the relative humidity and temperature are taken throughout the interior of the structure under test (step 12). The relative humidity and temperature measurements are made to determine grains per pound. Moisture content readings may be made, for example, with a GE Protimeter MMS Plus model by GE Protimeter, 500 Research Drive, Wilmington, Mass., US, or the Tramex Moisture Meter, from Tramex Ltd. of Dublin, Ireland moisture meter in the preferred embodiment.

In making the measurements, test sites are selected to be places where moisture might typically exist throughout the structure, including but not limited to openings such as window frames, door frames, electrical outlets and the like. In buildings where a vapor barrier is present, any location where the vapor barrier might have been cut is measured. Further, measurements are taken along the floor, floor boards and baseboards, walls and ceiling. Typically a measurement every 1 to 2 feet would be sufficient.

After measurements have all been taken, typically in each room, for example, the measurement meter is connected to a computer and the data therein is uploaded to a database, for example, giving temperature, relative humidity, moisture content, grains per pound, etc., as well as the date and time of measurement. The computer may also include a printer or other I/O devices for printing or otherwise reporting data.

Next, in step 14, a report is made of the results. In a particular embodiment, this report comprises details of a number of things, including:
Relative Humidity;
Temperature;
Grains Per Pound (specific humidity);
Moisture content measurements taken.

A decision may now be made at decision block 15, whether interpretation of the moisture content measurements in the report is desired. If not, then the report certifies the measurements made and the process is then completed. The report certificate can advantageously include a print of the measurement data, showing all the measurement values, if desired.

If interpretation is desired, then next, in step 16, a determination is made based on the results of the report, whether the moisture level within the portion of the structure being tested (testing may be done on subsets of an entire building) is within a desired level (for example, under 20% or under 18% in particular embodiments). If so, then a moisture content level pass certificate is issued (step 18) which the building owner/builder/selling agent/buyer can then keep to establish the moisture content level. The process is then completed.

However, if at decision block 16, moisture content was not within the desired level, a determination may be made at block 20 as to whether a moisture content level fail certificate is to be issued. If so, then a moisture content level failure certificate is issued (step 22). In either case, the process is then completed.

Thus, in accordance with the system and method, a certificate is provided indicating that a structure has been tested as to its moisture content. Should moisture or mold problems arise later, however, the certificate holder has useful information to help locate the cause of the moisture or mold growth, or to identify lack of liability. It can also assist in determining the construction stage where the moisture damage or mold infestation was caused. Such certificate may be useful in obtaining more favorable insurance rates.

Additionally, the issuance of a failure certificate can be desirable and useful, when the certificate recipient is a party that is attempting to have moisture or mold remediation performed, or is attempting to prove the existence of the problem or to determine liability for remediation.

If a certificate is not issued, as a result of failing to pass, or if a failure certificate is issued, moisture removal may be performed as a remediation. Such moisture removal may be accomplished, as an example, in the manner described in co-pending U.S. patent application Ser. No. 10/621,859, filed concurrently herewith by the inventors of this present application, entitled MOISTURE REDUCTION AND MOLD AND MOISTURE DAMAGE PREVENTATIVE SYSTEM AND METHOD IN CONSTRUCTION, the disclosure of which is hereby incorporated by reference. Once such moisture removal is accomplished, the moisture content level certification process can be performed again, to then issue a certificate.

Further, a system according to a preferred embodiment of the present invention comprises a system and method for reducing moisture content in a building or portion of a building under construction, wherein said reduction is made as a curative and preventative measure that takes place at a specific phase in the construction process.

Figure 2:
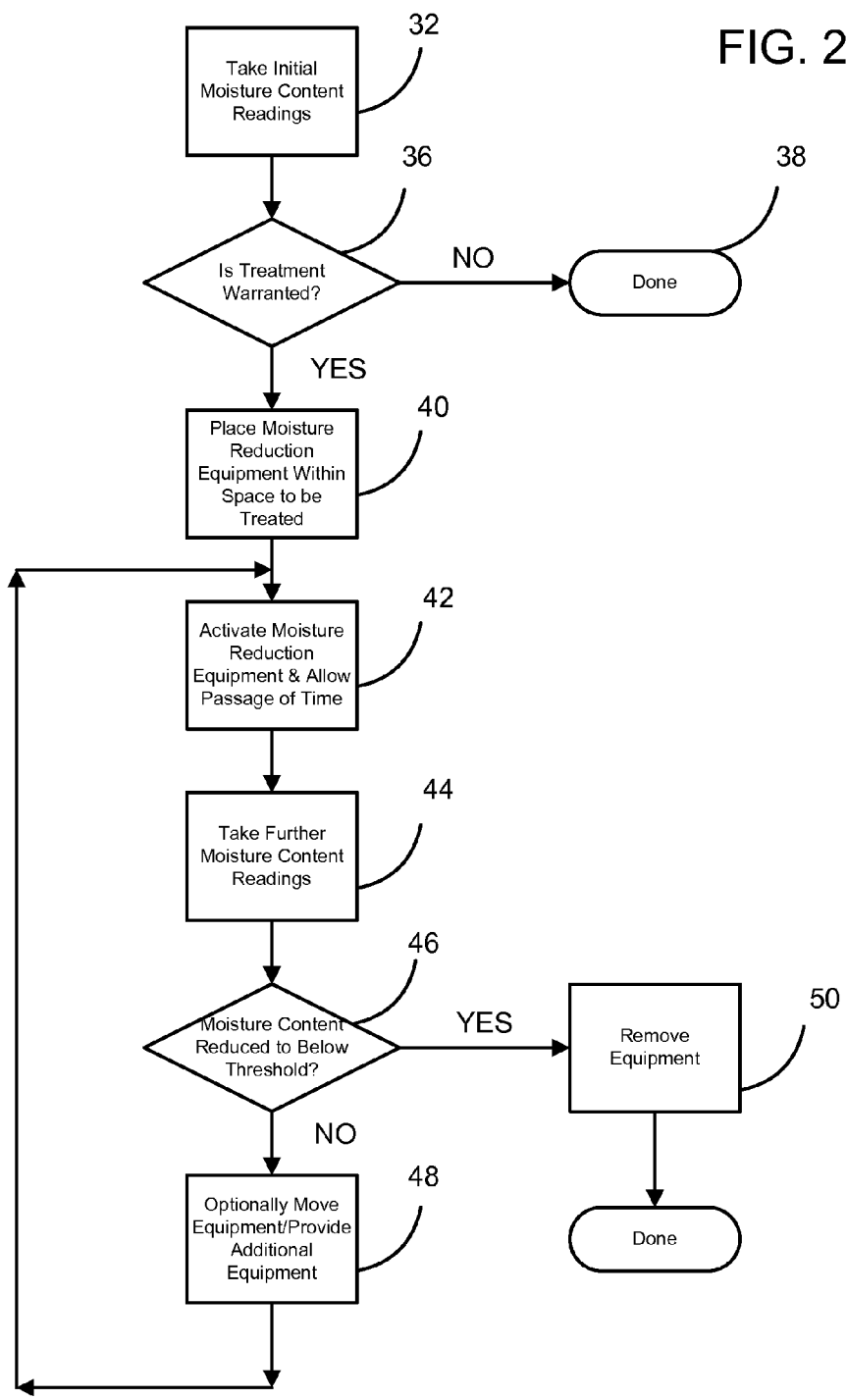
FIG. 2 is a block diagram of a process according to the present invention.

Referring now to FIG. 2, which is a block diagram of the moisture reduction process according to the present invention, the system and method are typically employed, in the case of construction, after the roof, windows and doors are installed and before the so called finish trades (wall board, insulation, cabinetry, etc.) are done. When a decision to take the preventative measure has been made, initial readings of moisture content of construction materials, relative humidity and temperature are taken in the building under test (step 32). These measurements are made to determine how to effect moisture removal in the building and may be made, for example, with a GE Protimeter MMS Plus model by GE Protimeter, 500 Research Drive, Wilmington, Mass., US, or the Tramex Moisture Meter, from Tramex Ltd. of Dublin, Ireland moisture meter in particular embodiments.

Next, in step 36, a determination is made based on the results of the readings, whether preventative moisture removal is warranted. For example, if moisture content of Douglas fir is below 20% moisture content, moisture removal treatment may not be needed. If further treatment is not needed, then the process is complete at block 38. However, if further treatment is deemed advisable, then the process continues to block 40, wherein moisture reduction equipment is placed within the space that is to be treated. The specific moisture reduction equipment employed can vary based on the moisture removal needs of the structure, but typically will include air moving equipment, such as blowers, for circulating the air within the space, dehumidifiers to extract the moisture from the air and either contain it within the dehumidifier or dispose of it external to the space (by a drain tube, for example). Additionally, heating equipment may be employed, to raise the temperature within the space to increase the speed of moisture removal.

Examples of typical equipment that may be employed in the system and performing the method is as follows:

Blower: An electric portable blower that provides a continuous, high velocity airflow, such as model #797 Ace TurboDryer, from Dri-Eaz of Burlington, Wash., US, or the Dri-Eaz Santana SX model turbodryer, or the Gale Force air mover by Dry Air Technology of Burlington, Wash.

Dehumidifier: #721 DrizAir 1200, by Dri-Eaz of Burlington, Wash., US. This is a refrigerant dehumidifier which provides a 15 gallon per day maximum moisture removal output level, while drawing 6.4 amps current at 120V. Also, the DrizAir 2000, a 25 gallon per day model can be employed. Alternatively, a DriTec desiccant dehumidifier may be employed, which uses silica gel to absorb moisture from the air, manufactured by Dri-Eaz of Burlington, Wash.

Heater: portable heaters, such as propane/natural gas powered heaters, such as the Dri-Eaz K85 mobile furnace, by Dri-Eaz of Burlington, Wash., US.

In a typical installation, four or five blowers or fans will be grouped together with one dehumidifier and heater in a given space.

Depending on the particular characteristics of the space being treated, openings into other rooms or other parts of a building are sealed off with some sort of vapor barrier (for example, plastic sheeting in roll form and duct tape to seal the sheeting to close off the opening). Also, window or door openings that do not yet have the windows or doors installed may be sealed in corresponding fashion.

Once the equipment is in place, the blowers and dehumidifier are activated (and heaters, if present) and they are allowed to run for a period of time (block 42), typically a 24 hour period, whereupon further moisture readings are taken (block 44) to track the progress of moisture removal. At decision block 46, a determination is made whether sufficient moisture has been removed from the space. If not, then the equipment is allowed to continue to operate. Optionally, the equipment may be moved around to different locations within the space being treated (block 48). The process loops back to allow the passage of time at block 42, and the time/readings/determine whether acceptable moisture content reduction has occurred cycle continues until the result of the decision block 46 is that yes, the moisture content has been reduced to an acceptable level (for example, 20% or lower moisture content). Then the moisture removal process is completed and the equipment is removed (block 50).

A typical time between the initial placement of the equipment and determination that the space has a sufficiently low moisture content level is 4 to 7 days. Of course this depends on a number of factors, including the initial moisture content of the space, the capacity of the moisture control equipment that is installed, and relative humidity and temperature, for example.

Some other possible variations in the process can occur. For example, if at block 44, when further readings are taken after the passage of time, it is determined that the moisture level is not being reduced (or is not being reduced at a sufficient rate), then additional blower/dehumidifier/heating equipment may be added. Further, if after a passage of time, the moisture levels are not reducing in a desired fashion, this typically indicates that moisture is leaking into the space from an outside source (for example an improperly installed roof is leaking) and investigation of the source of the moisture should be made.

Examples of application of the system and method are given below. The measurement goal for all tests in these particular examples is 18% moisture content:

Example 1

New construction, 1500 square feet.

Day 1, temperature 71.5° F., 36.7% relative humidity. 2 measurements were taken low along wall studs, giving 16 and 18% moisture content. 4 measurements were taken high along wall studs, giving 16, 24, 21 and 21%.

Moisture removal equipment was installed and allowed to run for the rest of day 1. On day 2, temperature was 64.7° F., 46.9% relative humidity. 2 measurements were taken low along wall studs, giving 16 and 18% moisture content. 4 measurements were taken high along wall studs, giving 16, 18, 18 and 18% moisture content. The moisture removal operation was judged completed.

Example 2

New construction, 2200 square feet.

Day 1, temperature 69.4° F., 49.1% relative humidity. 7 measurements were taken low along wall studs, giving 25, 20, 25, 25, 15, 25 and 22% moisture content. 7 measurements were taken high along wall studs, giving 21, 19, 25, 25, 25, 25 and 25%.

Moisture removal equipment was installed and allowed to run. On day 2, temperature was 65.1° F., 55.3% relative humidity. 7 measurements were taken low along wall studs, giving 20, 17, 25, 25, 20, 21 and 20% moisture content. 7 measurements were taken high along wall studs, giving 22, 18, 23, 23, 15, 21 and 20% moisture content. The moisture removal operation was continued, and then further measurements were taken on day 3. 6 lower level measurements of 20, 18, 18, 18, 15 and 21% moisture content were taken, and 7 upper level measurements of 18, 17, 20, 23, 18, 18 and 20% were recorded. Moisture removal was continued and on day 4, 7 measurements were taken at both lower and upper levels, resulting in: lower 18, 18, 18, 18, 15, 18, 17; and upper 16, 16, 17, 16, 18, 16, 15. The moisture removal operation was judged completed at this state.

Example 3

New construction, 2300 square feet.

Day 1, temperature 63.2° F., 38.0% relative humidity. 7 measurements were taken low along wall studs, giving 15, 20, 15, 15, 30, 30, and 16% moisture content. 7 measurements were taken high along wall studs, giving 30, 30, 30, 18, 25, 24 and 20%.

Moisture removal equipment was installed and allowed to run until day 2, when further measurements are made, temperature was 80.2° F., 29.5% relative humidity. Measurements low along wall studs were 15, 15, 15, 15, 20, 15 and 16% moisture content. High location measurements were 25, 20, 25, 18, 23, 20 and 20% moisture content. The moisture removal operation was continued until day 3, when measurements as follows were judged to have sufficiently accomplished the desired moisture removal: low, 15, 15, 15, 15, 18, 15, 16%; and high 18, 17, 18, 18, 16, 15, 18%.

Example 4

New construction, 1500 square feet.

Day 1, temperature 68.8° F., 43.0% relative humidity. 4 measurements were taken low along wall studs, giving 21, 18, 15 and 17% moisture content. 7 measurements were taken high along wall studs, giving 15, 25, 25, 21, 16, 15 and 18%.

Moisture removal equipment was installed and allowed to run. On day 2, when further measurements are made, temperature was 58.4° F., 59.4% relative humidity. Measurements low along wall studs were 18, 18, 15 and 17% moisture content. High location measurements were 15, 18, 18, 17, 16, 15 and 18% moisture content. This was sufficient moisture removal to complete the operation.

Example 5

New construction, 2150 square feet.

Day 1, temperature 57.4° F., 97.4% relative humidity. 7 measurements were taken low along wall studs, giving 20, 15, 20, 21, 40, 18 and 16% moisture content. Measurements taken high along wall studs were 20, 20, 23, 40, 22, 17 and 30%.

Moisture removal equipment was installed and allowed to run until day 2, when further measurements are made, temperature was 67.0° F., 47.9% relative humidity. Measurements low along wall studs were 15, 15, 15, 15, 18, 18 and 16% moisture content. High location measurements were 15, 15, 18, 16, 15, 17 and 17% moisture content. This was a sufficient moisture level to complete the operation.

Example 6

New construction, 2500 square feet.

Day 1, temperature 68.0° F., 36.6% relative humidity. 7 measurements were taken low along wall studs, giving 13, 11, 12, 11, 11, 13 and 10% moisture content. Measurements taken high along wall studs were 12, 11, 13, 10, 12, 13 and 11%.

Since all measurements were below the target level, no moisture removal was performed as the area was already at a sufficiently low moisture content.

In making measurements, any wood surfaces are measured, but typically moisture content measurements are made at base plates, studs and floors. It is not necessary to measure every stud in the structure, because if a stud with moisture content above the moisture threshold is detected in an area, then moisture removal will be performed in the area, so it isn't required to keep measuring at that point. Thus, for example, if the first set of measurements taken is beyond the acceptable moisture threshold, taking additional measurements is not necessary, but can be completed if desired, to provide historical data for comparison when the moisture removal is completed, and more measurements might be taken to further show overall moisture levels. Thus, in performing the process, typically moisture content tests are made throughout the structure, but moisture removal is only needed to be done in those areas where the moisture content level is too high.

Thus, in accordance with the system and method, a preventative moisture removal is accomplished to bring the moisture content level within a space to a desired level below that which would support mold growth, to reduce the likelihood that mold or moisture damage problems will arise in the finished construction. Should mold or moisture damage problems arise later, however, the builder has useful information to help locate the cause of the mold growth or moisture damage, as it is known from the use of the system and method that at a crucial point in the construction process, the moisture content level had been reduced sufficiently to prevent such growth or water damage. This information can help in determining what party might bear the responsibility for costs involved in mold or moisture damage remediation procedures. It can also assist in determining the construction stage at which a mold infestation or moisture entry took place.

While in the preferred embodiment, the moisture content level of 20% is a desired threshold, applied to Douglas fir wood, for example, below which the moisture content is desirably reduced, and while 18% was given as the threshold level in the illustrative examples herein, different levels may be appropriate in other types of wood and in other materials such as engineered woods (oriented strand board, plywood, fiberboard, etc.), wallboard or other materials.

While a preferred embodiment of the present invention has been shown and described, it will be apparent to those skilled in the art that many changes and modifications may be made without departing from the invention in its broader aspects. For example, while the preferred embodiments relate to desired moisture content levels being below a desired threshold, alternate embodiments include situations where the pass or failure of a moisture content analysis depends on the moisture content being above a desired threshold level or within a desired range. The appended claims are therefore intended to cover all such changes and modifications as fall within the true spirit and scope of the invention.

What is claimed is:

1. A method for certifying a moisture content level, comprising:
    measuring, with a moisture meter, moisture content at a plurality of interior locations within a building;
    comparing the measured moisture content with a threshold moisture content level;
    drying, with at least one drying device, a space of the building in order to reduce the moisture content at the plurality of interior locations, wherein the at least one drying device is located within the building while drying the space; and
    measuring, with the moisture meter, moisture content at one or more of the plurality of interior locations to confirm that the moisture content is below the threshold moisture content level.

2. The method of claim 1, further comprising determining a construction stage where the moisture content was introduced to the plurality of interior locations, based at least in part on the measured moisture content.

3. The method of claim 1, further comprising:
    measuring a temperature at the plurality of interior locations;
    measuring a relative humidity at the plurality of interior locations; and
    determining grains per pound of moisture content at the plurality of interior locations based, at least in part, on the measured temperature and the measured relative humidity, wherein comparing the measured moisture content comprises comparing the grains per pound of moisture content with the threshold moisture content level.

4. The method of claim 1, wherein the space of the building is surrounded by a vapor barrier prior to using the at least one drying device to remove the moisture content.

5. The method of claim 4, wherein the at least one drying device is located within the vapor barrier while drying the space.

6. The method of claim 1, wherein the plurality of interior locations comprise a window frame and a door frame.

7. The method of claim 1, wherein the plurality of interior locations comprise at least one exposed wall stud.

8. The method of claim 7, wherein the plurality of interior locations comprise both a high location of the at least one exposed wall stud and a low location of the at least one exposed wall stud.

9. The method of claim 8, wherein the high location is near a ceiling or near a roof of the space.

10. The method of claim 8, wherein the low location is near a floor of the space.

11. A system, comprising:
    means for measuring moisture content at a plurality of interior locations within a building;
    means for comparing the measured moisture content with a threshold moisture content level associated with a moisture content level certification; and
    means for drying a space of the building in order to reduce the moisture content at the plurality of interior locations, wherein the means for drying is located within the building while the space is being dried, and wherein at least one of the plurality of interior locations is again measured for moisture content to confirm that the moisture content is below the threshold moisture content level.

12. The system of claim 11, wherein the space comprises the building, and wherein the building is substantially sealed relative to outside of the building.

13. The system of claim 11, wherein the space comprises one or more rooms of the building, and wherein the one or more rooms are substantially sealed relative to other rooms of the building.

14. The system of claim 11, wherein the means for drying is entirely located within the space.

15. The system of claim 11, wherein the means for drying comprises means for drying, prior to said measuring, the space of the building in a first drying operation, and wherein the moisture content is measured after the first drying operation is completed.

16. The system of claim 15, wherein the means for comparing comprises means for determining whether a second drying operation is required in order to further reduce the moisture content.

17. The system of claim 11, wherein the means for measuring comprises means for measuring the moisture content at multiple locations of at least one exposed wall stud in the space.

18. The system of claim 17, wherein the multiple locations comprise both a high location of the at least one exposed wall stud and a low location of the at least one exposed wall stud.

19. The system of claim 18, wherein the high location is near a ceiling or near a roof of the space.

20. The system of claim 18, wherein the low location is near a floor of the space.

* * * * *